United States Patent [19]

Delavarenne et al.

[11] Patent Number: 4,840,750

[45] Date of Patent: Jun. 20, 1989

[54] CATALYTIC PROCESS FOR THE MANUFACTURE OF ACID FLUORIDE

[75] Inventors: Serge Delavarenne, Saint Germain En Laye; Michel Fauconet, St. Avold; Michel Simon, Harnes; Jean Sommer, Strasbourg, all of France

[73] Assignee: Societe Chimique des Charbonnages S.A., Tour Aurore, France

[21] Appl. No.: 121,642

[22] Filed: Nov. 16, 1987

[30] Foreign Application Priority Data

Nov. 20, 1986 [FR] France .............................. 86 16143
Feb. 19, 1987 [FR] France .............................. 87 02140
Jul. 24, 1987 [FR] France .............................. 87 10567

[51] Int. Cl.$^4$ ............................................. C07C 51/58
[52] U.S. Cl. ............................. 260/544 A; 260/543 F; 260/544 F
[58] Field of Search ........................ 260/544 A, 544 F

[56] References Cited

U.S. PATENT DOCUMENTS

| | | | |
|---|---|---|---|
| 4,495,110 | 1/1985 | Corn .................................. | 260/544 A |
| 4,499,029 | 2/1985 | Scaccia et al. ..................... | 260/544 A |
| 4,582,571 | 4/1986 | Grimm et al. ..................... | 260/544 A |

*Primary Examiner*—Paul J. Killos
*Attorney, Agent, or Firm*—Finnegan, Henderson, Farabow, Garrett & Dunner

[57] ABSTRACT

Catalytic process for the manufacture of acid fluoride from carbon monoxide, hydrogen fluoride, and an aliphatic hydrocarbon stream mainly containing at least one alkane containing 3 to 4 carbon atoms, comprising the following series of stages:

(a) introduction of at least one fluid chosen from carbon monoxide and the hydrocarbon stream into a reactor in the presence of a superacidic catalyst system consisting essentially of hydrogen fluoride and antimony pentafluoride, (b) where appropriate, if it has not already been introduced during stage (a), introduction into the reactor of a fluid chosen from carbon monoxide and the hydrocarbon stream, the reactor being at a temperature not above 60° C. to permit the formation, principally, of a complex consisting of the alkyloxocarbonium cation and the anion $SbF_6^-$, (c) conversion of the complex into acid fluoride, (d) separation of the acid fluoride, and (e) recovery of the superacidic catalyst system.

The process is applicable to the manufacture of methylmethacrylate.

12 Claims, No Drawings

CATALYTIC PROCESS FOR THE MANUFACTURE OF ACID FLUORIDE

BACKGROUND OF THE INVENTION

There is already a known process for the preparation of isobutyryl fluoride from an anhydrous mixture of propylene, carbon monoxide, and hydrogen fluoride. In particular, U.S. Pat. No. 4,499,029 discloses passing such a mixture through at least two reaction zones arranged in series and adding to the reaction mixture, between the reaction zones, progressive quantities of anhydrous propylene and carbon monoxide, the process being carried out with a residence time of 15 seconds to 10 minutes in the reaction zones, at a pressure of 1 to 150 bars and a temperature of 0° to 100° C., the molar relationship $C_3H_6/CO/HF$ in the reaction mixture being between 1/5/5 and 1/30/200. However, the cost of manufacture of isobutyryl fluoride produced in this manner is fairly high, given that the starting material in this process, namely propylene, is itself produced by dehydrogenation of alkanes from oil cuts or by steam cracking of hydrocarbons.

It is already known, from H. Hogeveen and C. F. Roobeek, *Rec. Trav. Chim. Pays-Bas.* 91 (1972), pages 137–40, to react at 0° C. an equimolar mixture of n-butane and carbon monoxide in the presence of antimony pentafluoride $SbF_5$ in solution in $SO_2ClF$. This reaction leads to the formation of a mixture of sec-butyloxocarbonium (74%), tertbutylcarbonium (25%) and tertbutyloxocarbonium (1%) ions. From the same document, it is known to carbonylate propane at 0° C., in a solvent ($SO_2ClF$) and in the presence of antimony pentafluoride, the molar relationship $C_3H_8/CO$ being between 1 and 9. It is also known, from N. Yoneda et al, *Chemical Letters* (*Chemical Society of Japan*), (1983), pages 17–18, to carbonylate branched alkanes containing at least 5 carbon atoms, at a temperature of 30° C., in the presence of the superacid $HF-SbF_5$ (molar relationship $HF/SbF_5$ equal to 5), the molar relationship alkane/HF being equal to 0.1. Furthermore, it is known from G. Olah et al, *Journal of the American Chemical Society*, 95, pages 4939 et seq., that:

At a temperature between −10° C. and −103° C., in a solvent ($SO_2ClF$) and in the presence of the superacid $HSO_3F-SbF_5$, an equilibrium is established between propane and the isopropyl cation, and At a temperature of −78° C., in a solvent ($SO_2ClF$) and in the presence of a superacidic system comprising hydrogen fluoride and antimony pentafluoride, an equilibrium is established between 2-methylpropane (or isobutane) and the trimethylcarbenium ion.

E. Hogeveen has already described in *Adv. Phys. Org. Chem.*, 10, 32 (1973) the decarbonylation reaction of the pivaloyl cation at −70° C., either in an equimolar mixture of hydrogen fluoride and antimony pentafluoride or in a mixture of 2 parts by volume of $SO_2ClF$ per 1 part by volume of antimony pentafluoride, to form the tert-butyl cation.

It will be noted that, in general, these prior documents are concerned exclusively with the kinetics of protonation of alkanes or of decarbonylation at a very low temperature and do not describe any covalent species capable of being obtained by employing these reactions. In particular, none of them describe the production of acid fluorides. Furthermore, none of them have demonstrated the possibility of regenerating the superacid employed for the protonation.

Furthermore, U.S. Pat. No. 4,582,571 discloses the possibility of forming isobutyryl fluoride by reaction of carbon monoxide, propane, anhydrous hydrogen fluoride, and antimony pentafluoride at a pressure above 100 bars and at a temperature close to 100° C. However, on the one hand this document is silent on the respective proportions of the various reactants and on the other hand discloses pressure and temperature conditions that are too severe for industrial use. Additionally, it has been discovered that the nature of the acid fluoride formed by such a process surprisingly depends on the value of the ratio CO/propane.

SUMMARY OF THE INVENTION

The problem that the present invention strives to solve is the manufacture of an acid fluoride from an alkane (propionyl and isobutyryl fluorides from propane, pivaloyl fluoride from isobutane) by a process that does not present either the disadvantage (referred to earlier) of the high cost of manufacture of the starting material, since the alkane is extracted directly from oil cuts, or the other disadvantage of the too severe temperature conditions of U.S. Pat. No. 4,582,571. Additional objects and advantages of the invention will be set forth in part in the description that follows, and in part will be obvious from the description, or may be learned by practice of the invention. The objects and advantages of the invention may be realized and attained by means of the instrumentalities and combinations particularly pointed out in the appended claims.

In a first stage, the applicants undertook the study of the carbonylation of alkanes containing 3 to 4 carbon atoms in the presence of various superacidic systems in order to determine a system capable of leading to the production of acid fluorides in an efficient and economical manner. In a second stage, the applicants undertook the study of the separation of the compound produced in order to determine the means capable of ensuring the regeneration of the chosen superacid as efficiently as possible.

To achieve the foregoing objects and in accordance with the purpose of the invention, as embodied and broadly described herein, the process of the invention comprises a catalytic process for the manufacture of acid fluoride from carbon monoxide, hydrogen fluoride, and an aliphatic hydrocarbon stream consisting essentially of at least one alkane containing 3 to 4 carbon atoms, comprising the following sequential steps:

(a) introducing at least one fluid selected from the group consisting of carbon monoxide and the hydrocarbon stream into a reactor in the presence of a superacidic catalyst system consisting essentially of hydrogen fluoride and antimony pentafluoride, (b) if it has not already been introduced during step (a), introducing into the reactor a fluid selected from the group consisting of carbon monoxide and the hydrocarbon stream, the reactor being at a temperature not above 60° C. permitting the formation, principally, of a complex consisting of the alkyloxocarbonium cation and the anion $SbF_6^-$, (c) converting the complex into acid fluoride, (d) separating the acid fluoride, and (e) recovering the superacidic catalyst system.

In one preferred embodiment in accordance with the invention, the process further comprises (f) adjusting the quantity of hydrogen fluoride to the constitution of the superacidic catalyst system employed in step (a).

DESCRIPTION OF THE PREFERRED EMBODIMENTS

Reference will now be made in detail to the presently preferred embodiments of the invention.

The process according to the invention necessarily comprises the four stages denoted (a), (c), (d), and (e). In this case, carbon monoxide and the stream containing principally alkane are introduced simultaneously into the reactor. Alternatively, it may be unnecessary to bring carbon monoxide simultaneously with the stream containing principally alkane into contact with the superacidic catalyst system. In this second case, the carbon monoxide and the hydrocarbon stream will be introduced into the reactor separately by virtue of the additional stage (b).

As used herein:
"principally alkane" means that the aliphatic hydrocarbon stream may contain, besides the alkane (propane, n-butane, or isobutane), small proportions of alkenes or alkynes containing a low number of carbon atoms, such as particularly butene, propyne, or propylene;
"principally alkyloxocarbonium cation" means that the reaction generated by the superacidic catalyst system according to the invention leads essentially to the formation of this cation, in addition to minor proportions of carbocations that either are derived from the other aliphatic hydrocarbons that may be present in the reaction mixture or that originate from rearrangements of the carbocations or of the alkyloxocarbonium cation. Thus, the isopropyloxocarbonium (also called isobutyryl) cation can, under certain conditions, be formed from propane, the ethyloxocarbonium (also called propionyl) cation is formed from propane, and the tertbutyloxocarbonium (also called pivaloyl) cation is formed from isobutane.

In accordance with the present invention, as embodied herein, stage or step (a) is intended to bring either carbon monoxide, or the stream containing principally alkane, or their mixture, into contact with the superacidic catalyst system according to the invention. This contact takes place in a reactor that may be of an autoclave type or else of tubular type or of any other type suitable for bringing the reactants into contact. Furthermore, at the time when the reactant(s) is (or are) introduced into the reactor, the latter already contains the catalyst system comprising hydrogen fluoride and antimony pentafluoride $SbF_5$ in such proportions that they form a homogeneous phase.

During stage (b), which is, as indicated earlier, optional, the other component is introduced into the reactor. As embodied herein, it is only from this moment onwards that, with carbon monoxide and alkane being in contact with the superacidic catalyst system, a complex consisting of the alkyloxocarbonium cation and of the $SbF_6^-$ anion will begin principally to form. The presence of this cation is confirmed by sampling and analysis of the reaction mixture at this stage, particularly by proton nuclear magnetic resonance. This analysis produces a spectrum containing:
in the case of the propionyl cation: a triplet at about 2.2 ppm (3H) and a quadruplet at about 4.3 ppm (2H);
in the case of the isobutyryl cation: a doublet at about 2.1 ppm (6H) and a heptuplet at about 4.4 ppm (1H); and
in the case of the pivaloyl cation: a singlet at about 2.0 ppm (9H).

In order for the formation of the complex to take place as efficiently as possible, it is desirable that the operating conditions in the reactor be chosen as follows:
a molar relationship CO/alkane at least equal to about 0.1 and preferably of between approximately 0.1 and 30; when the alkane is propane, a molar relationship CO/propane greater than 7/3 permits mainly the formation of propionyl fluoride whereas a molar relationship not greater than 7/3 permits mainly the formation of isobutyryl fluoride,
a molar relationship $HF/SbF_5$ of between approximately 1 and 30,
a temperature between approximately $-80°$ C. and $+60°$ C.

The complex formed at the end of stage (b) is employed for the manufacture of the acid fluoride in a good yield, particularly by virtue of the embodiments described below.

According to a first embodiment of the process according to the invention, the complex is converted into acid fluoride by intervention of at least one means for shifting the equilibrium between the complex and the acid fluoride towards the formation of the latter. Among the means of intervention for shifting this chemical equilibrium, within the scope of stage (c), particular mention may be made of the addition of a chemical species capable of significantly reducing the acidity of the reaction mixture. Hydrogen fluoride will preferably be chosen among such species. Means of intervention of a physical, for example thermal, nature may also be envisaged within the scope of stage (c).

When the above-mentioned chemical equilibrium has been sufficiently shifted, a substantial proportion of the acid fluoride has then to be separated from the remaining constituents of the reaction mixture in stage (d). Knowing the boiling points at atmospheric pressure of hydrogen fluoride (20° C.), of antimony pentafluoride (150° C.), and of the acid fluoride (60° C. in the case of isobutyryl fluoride, for example), and the respective quantities of the various components present, the person skilled in the art is capable of choosing the most appropriate method of separation.

Still within the scope of this first embodiment, the process according to the present invention additionally provides for the superacidic catalyst system and, if desired, the residual acid fluoride to be recovered during stage (e). When the process is carried out noncontinuously, the superacidic catalyst system, by itself or mixed with hydrogen fluoride and, if desired, a part of the acid fluoride that has not been separated, is recovered to be reused in the next reaction. When the process is carried out continuously, the superacidic catalyst system, mixed, where appropriate, with hydrogen fluoride and/or the acid fluoride, is recycled to the reactor. When hydrogen fluoride has been added during stage (c), recycling may be carried out after partial removal of hydrogen fluoride. In this case, a special embodiment resides in adjusting, by virtue of stage (f), the quantity of hydrogen fluoride to the constitution of the superacidic catalyst system employed in stage (a). The hydrogen fluoride removed at this stage may, in its turn, be recycled, for example to the point of intervention in stage (c), where it will permit at least partially to form the addition required to shift the chemical equilibrium mentioned earlier.

The reaction of the process according to the present invention may be conveniently carried out at atmospheric pressure. For reasons of kinetics and of economy in industrial use, it may also be advantageous to operate at a pressure above atmospheric pressure, for example at a pressure of up to about 250 bars and preferably not greater than about 40 bars. Depending on the pressure, the person skilled in the art is capable of selecting, on the one hand, the residence time of the reaction mixture in the reactor and, on the other hand, the appropriate temperature. The residence time in the reactor is generally between about 0.1 and 300 minutes. Moreover, in the case where the reaction pressure is markedly higher than atmospheric pressure, it may be desirable to reduce the pressure at the end of stage (c) and to recompress the fluids recovered particularly during stage (e) and, where appropriate, during stage (f) up to reactor pressure.

The process according to the invention makes it possible to obtain, with satisfactory kinetics and in satisfactory yield, after at least one purification stage well-known to those skilled in the art, such as fractional distillation, acid fluoride of a degree of purity that is suitable for subsequent uses. In fact, the acid fluoride constitutes a synthesis intermediate permitting, in particular, the corresponding carboxylic acid to be produced by hydrolysis. For example, isobutyryl fluoride is a particularly important synthesis intermediate permitting, in particular, the production of methacrylic acid successively by hydrolysis to isobutyric acid and then oxydehydrogenation of the latter or else the production of methyl methacrylate by methanolysis to methyl isobutyrate and then oxydehydrogenation of the latter. In accordance with the objective of the present invention, these compounds are produced at a moderate cost of manufacture by virtue of the choice of an alkane as the initial raw material.

The examples below are intended to illustrate the present invention without limiting its scope in any way.

EXAMPLES 1 TO 4

Antimony pentafluoride and hydrogen fluoride in a molar relationship $HF/SbF_5$ equal to 4 are introduced at 20° C., with stirring and under a nitrogen atmosphere, into a polymonochlorotrifluoroethylene reactor of 0.1 liter capacity. This mixture is then transferred into a stainless steel autoclave reactor of 0.3 liter capacity. The temperature T of the mixture (expressed in degrees Celsius) is then adjusted to the value shown in Table I and then the mixture of propane and carbon monoxide in the molar relationship $CO/C_3H_8$ shown in Table I is introduced by a turbine until it reaches the pressure P mentioned in the table (expressed in bars). Two operating regimes can then be applied, namely:

a "static" regime (marked s): in this case, all the reactants are introduced at the beginning and the pressure shown in Table I is the initial pressure, or else a "dynamic" regime (marked d): in this case, the addition of propane and of carbon monoxide continues throughout the reaction with a time of contact between the gas and the liquid phase of about 9 seconds, the pressure indicated in the table being constant throughout the test.

In each case the duration of the test is 1 hour. At the end of the test ("static" regime) or during the test ("dynamic" regime), the gaseous phase is released at a temperature not exceeding 25° C. and is analysed in line with a series of chromatographs making it possible to identify and determine:

on the one hand, the unreacted propane and carbon monoxide so as to calculate the degree of conversion D.C. (expressed in % and shown in the table below) equal to the number of moles of propane consumed over the number of moles of propane added;

on the other hand, the secondary gaseous products resulting from the reaction, generally forming a mixture of hydrogen, methane, and ethane whose molar proportions in the mixture are those shown in Table I below.

Furthermore, the liquid phase present in the reactor is subjected to a total hydrolysis at 0° C., and then the aqueous solution obtained is analyzed by gas phase chromatography so as to identify and determine the organic acids formed by hydrolysis of the reaction products. These generally form a mixture of isobutyric acid (IBA), of propionic acid (PA), and of diverse compounds (shown together as "others" in Table I below), these including in particular acetic acid, n-butyric acid, methanol, and acetone. The molar proportions of the acids IBA and PA in the mixture are shown in Table I below.

EXAMPLES 5 TO 9

A polymonochlorotrifluoroethylene reactor 3 ml in capacity, equipped with two taps and containing a mixture of hydrogen fluoride and antimony pentafluoride in a molar proportion $HF/SbF_5$ equal to 3.8, has a polymonochlorotrifluoroethylene dip tube through which a mixture of carbon monoxide and propane in a molar relationship $CO/C_3H_8$ shown in the table below is introduced at a rate of 210 ml/hour (Example 5 is comparative). This reactor is maintained at atmospheric pressure and, by virtue of a brine bath, at a temperature of $-10°$ C. Gas circulation is provided by a peristaltic pump via a circuit consisting of polytetrafluoroethylene tubing. At the outlet of the reactor, a condenser surrounding the tubing is supplied with an acetone-solid carbon dioxide mixture by a pump, in order to condense the hydrogen fluoride vapor that might escape from the mixture. Downstream of this tube, a polytetrafluoroethylene soda lime trap enables the last traces of hydrogen fluoride to be trapped. After 60 minutes' operation, the reactor's dip tube is used to withdraw a fraction of the liquid phase for analysis by proton nuclear magnetic resonance. This analysis makes it possible to identify the cations formed during the reaction. The nuclear magnetic resonance spectrum obtained (signals at 2.1 ppm and 4.4 ppm) reveals the presence of isobutyryl and propionyl cations and makes it possible to determine their respective proportions, which have been shown under the headings IBA and PA in Table II below. After 60 minutes' reaction a quantity of anhydrous hydrogen fluoride is added to the liquid phase obtained, such that the molar relationship $HF/SbF_5$ becomes equal to 54. A fraction of the phase thus obtained is withdrawn again for analysis by proton nuclear magnetic resonance. The spectrum obtained (signals at 1.8 ppm and 3.5 ppm) reveals, inter alia, the presence of isobutyryl fluoride.

TABLE II

| Example | $CO/C_3H_8$ | IBA | PA |
| --- | --- | --- | --- |
| 5 | 3.0 | 41 | 59 |

TABLE II-continued

| Example | CO/C₃H₈ | IBA | PA |
| --- | --- | --- | --- |
| 6 | 2.0 | 55 | 45 |
| 7 | 1.0 | 89 | 10 |
| 8 | 0.5 | 96 | 2 |
| 9 | 0.1 | 97 | 2 |

EXAMPLE 10

A polymonochlorotrifluoroethylene reactor, 3 ml in capacity, containing a mixture of hydrogen fluoride and antimony pentafluoride in a molar relationship $HF/SbF_5$ equal to 7:3 has a polymonochlorotrifluoroethylene dip tube through which a mixture of carbon monoxide and n-butane in a molar proportion $CO/C_4H_{10}$ equal to 3 is introduced at a rate of 210 ml/hour. This reactor is maintained at atmospheric pressure and, by virtue of a brine bath, at a temperature of $-10°$ C. Gas circulation is provided by a peristaltic pump via a circuit consisting of polytetrafluoroethylene tubing. At the outlet of the reactor, a condenser surrounding the tubing is supplied with ethanol by a cryostat, in order to condense the hydrogen fluoride vapor that might escape from the mixture. Downstream of this tube, a polytetrafluoroethylene soda lime trap enables the last traces of hydrogen fluoride to be trapped. After 60 minutes' operation, the reactor's dip tube is used to sample a fraction of the liquid phase for analysis by proton nuclear magnetic resonance. This analysis makes it possible

- on the one hand, to determine the degree of conversion equal to the proportion of isobutane consumed relative to the quantity of isobutane introduced. This conversion is equal to 46% in this case;
- on the other hand, to identify the cations formed during the reaction. The nuclear magnetic resonance spectrum obtained (already described above) reveals the presence of pivaloyl, isobutyryl, and propionyl cations and makes it possible to determine their respective proportions:

| | |
| --- | --- |
| pivaloyl: | 88% |
| isobutyryl: | 2% |
| propionyl: | 4% |

These proportions are further confirmed by gas phase chromatographic analysis after trapping of the reaction mixture in a mixture of ethanol and sodium bicarbonate.

TABLE 1

| Example | T° C. | P | CO/C₃H₈ | D.C. | IBA | PA | Others | CH₄ | C₂H₆ | H₂ |
| --- | --- | --- | --- | --- | --- | --- | --- | --- | --- | --- |
| 1 | −6 | 55ˢ | 9.5 | 33 | 18 | 76 | 6 | 87 | 10 | 3 |
| 2 | −10 | 6ᵈ | 20.0 | 20 | 5 | 76 | 19 | 93 | 7 | 0 |
| 3 | +30 | 62ˢ | 16.0 | 94 | 12 | 79 | 9 | 89 | 7 | 4 |
| 4 | −10 | 6ᵈ | 3.3 | 10 | 23 | 66 | 11 | 79 | 21 | 0 |

It will be apparent to those skilled in the art that various modifications and variations could be made in the process of the invention without departing from the scope or spirit of the invention.

What is claimed is:

1. A catalytic process for the manufacture of acid fluoride from carbon monoxide, hydrogen fluoride, and an aliphatic hydrocarbon stream consisting essentially of at least one alkane containing 3 to 4 carbon atoms, comprising the following sequential steps:
   (a) introducing at least one fluid selected from the group consisting of carbon monoxide and said hydrocarbon stream into a reactor in the presence of a superacidic catalyst system consisting essentially of hydrogen fluoride and antimony pentafluoride,
   (b) if it has not already been introduced during step (a), introducing into the reactor a fluid selected from the group consisting of carbon monoxide and said hydrocarbon stream, the reactor being at a temperature not above 60° C. permitting the formation, principally, of a complex consisting of the alkyloxocarbonium cation and the anion $SbF_6^-$
   (c) converting said complex into acid fluoride,
   (d) separating said acid fluoride, and
   (e) recovering said superacidic catalyst system.
2. A process according to claim 1, wherein the molar relationship CO/alkane in the reactor is equal to at least 0.1.
3. A process according to claim 2, wherein the molar relationship CO/alkane in the reactor is between 0.1 and 30.
4. A process according to claim 2, wherein the molar relationship $HF/SbF_5$ in the reactor is between 1 and 30.
5. A process according to claim 4, wherein the reaction temperature is between $-80°$ C. and $+60°$ C.
6. A process according to claim 5, wherein the complex formed at the end of step (b) is converted into acid fluoride during step (c) by at least one means for shifting the equilibrium between said complex and said acid fluoride towards the formation of said acid fluoride.
7. A process according to claim 6, wherein said means for shifting is the addition of a chemical species capable of significantly reducing the acidity of the reaction mixture.
8. A process according to claim 7, wherein said chemical species is hydrogen fluoride.
9. A process according to claim 8, further comprising recycling said superacidic catalyst system recovered during step (e) to the reactor.
10. A process according to claim 9, further comprising partially removing hydrogen fluoride before recycling said superacidic catalyst system.
11. A process according to claim 10, further comprising recycling said removed hydrogen fluoride to the point of said at least one means for shifting in step (c).
12. A process according to claim 11, further comprising adjusting the quantity of hydrogen fluoride to the constitution of the superacidic catalyst system employed in step (a).

* * * * *